United States Patent [19]

Fernschild, deceased et al.

[11] Patent Number: 5,302,360

[45] Date of Patent: Apr. 12, 1994

[54] METHOD OF WORKING UP ANTIMONY HALIDE CATALYST SOLUTIONS

[75] Inventors: Guenter Fernschild, deceased, late of Hannover; Sarah Fernschild, heir, Hemmingen, both of Fed. Rep. of Germany, by Claudia Gerdau, legal representative

[73] Assignee: Kali-Chemie AG, Hannover, Fed. Rep. of Germany

[21] Appl. No.: 990,943

[22] Filed: Dec. 14, 1992

Related U.S. Application Data

[63] Continuation of Ser. No. 574,448, Aug. 29, 1990, abandoned.

[30] Foreign Application Priority Data

Sep. 2, 1989 [DE] Fed. Rep. of Germany ....... 3929263

[51] Int. Cl.$^5$ ............................................. C01G 30/00
[52] U.S. Cl. ....................................... 423/87; 502/24; 502/32
[58] Field of Search ...................... 502/24, 32; 423/87

[56] References Cited

U.S. PATENT DOCUMENTS

| | | | |
|---|---|---|---|
| 3,760,059 | 9/1973 | Ertel et al. | 423/87 |
| 3,784,671 | 1/1974 | Joerchel et al. | 423/88 |
| 3,787,557 | 1/1974 | Stewart | 423/87 |
| 3,806,589 | 4/1974 | Becher et al. | 423/491 |
| 4,005,176 | 1/1977 | Fernschild et al. | 423/87 |
| 4,722,774 | 2/1988 | Hyatt | 204/123 |

FOREIGN PATENT DOCUMENTS

| | | |
|---|---|---|
| 366366 | 10/1989 | European Pat. Off. |
| 2110797 | 9/1972 | Fed. Rep. of Germany |
| 2140188 | 2/1973 | Fed. Rep. of Germany |
| 2439540 | 12/1975 | Fed. Rep. of Germany |
| 1531799 | 11/1978 | United Kingdom |

Primary Examiner—Patrick P. Garvin
Attorney, Agent, or Firm—Evenson, McKeown, Edwards & Lenahan

[57] ABSTRACT

A method for working up antimony halide catalysts containing inactivating organic impurities having high boiling points, in which anhydrous antimony trichloride can be isolated in a technically simple manner. The antimony trichloride can be chlorinated to obtain antimony pentachloride which can be re-used as a catalyst in a fluorination process.

17 Claims, No Drawings

METHOD OF WORKING UP ANTIMONY HALIDE CATALYST SOLUTIONS

This application is a continuation of application Ser. No. 07/574,448, filed Aug. 29, 1990 and now abandoned.

BACKGROUND OF THE INVENTION

This invention relates to a method for working up inactive solutions containing antimony halide catalysts and organic impurities.

Fluorochlorohydrocarbons, fluorochlorocarbons, fluorohydrocarbons and fluorocarbons are used to a large extent as solvents and refrigerants. (For simplicity, the following description will refer only to hydrocarbon compounds, but this term is to be understood as including hydrogen-free compounds, perhaps more correctly called carbon compounds. Thus, as used herein, the term "fluorochlorohydrocarbon" should be understood as embracing halocarbons such as $CFCl_3$ as well as hydrogen-containing compounds.) In most industrial production processes, a chlorine/fluorine exchange takes place, catalyzed by antimony halide. Antimony pentahalide, particularly antimony pentachloride, is used as the catalyst.

The life of these catalysts is limited. During production of fluorochlorohydrocarbons or fluorohydrocarbons, unwanted halogenated organic compounds, some of which have considerably higher boiling points than the desired products, are also formed in addition to the desired process products. These byproducts dilute the antimony halide catalyst, so that gradually solutions containing antimony halide catalysts and organic impurities and having increasingly diminishing activity form. When the diminishing activity of the catalysts falls below a given limit, the inactive catalyst solution has to be removed from the reactor and be replaced by fresh antimony halide catalyst.

The solutions contain pentavalent and usually also trivalent antimony in the form of the halides, namely predominantly in the form of chlorides, but also to a greater or lesser extent in the form of mixed chlorides/fluorides. Depending on the field of use of the catalyst solution, the fluoride content may also be very low. In addition to the inorganic constituents, halogenated hydrocarbons are also present in the solutions. Which particular halogenated hydrocarbons are present in each case will naturally depend on the respective fluorination process in which the catalyst solution has been used and the manner in which the process is performed.

It is desirable to work up the inactive solutions for economic reasons (recovery of the antimony content), and also particularly for ecological reasons.

Antimony pentahalides and the halogenated hydrocarbons of the inactive solution form a homogenous mixture. Since some of the organic constituents have a boiling point similar to antimony pentachloride, for example, it is not possible to work up the solutions by means of distillation. Due to the formation of homogenous phases and the similar boiling points of antimony halides and impurities, it is difficult to separate the antimony halides from the organic constituents during working up.

Methods for working up inactive solutions containing antimony halide catalysts and organic impurities are already known. One method provides an aqueous work-up procedure. According to the process of British Patent Application No. GB 1,531,799, in order to separate the antimony halide from the organic constituents, sufficient water or aqueous hydrochloric acid is added to the organic solution containing antimony halide catalysts so that two liquid phases form. One phase is formed by the organic constituents, the other, aqueous phase contains the portions of pentavalent antimony. The hydrated antimony compounds can then easily be separated from the organic constituents and reduced if desired. The conversion of the dissolved antimony compounds into anhydrous compounds, in particular into the anhydrous antimony halides, is certainly very involved. Therefore the aqueous antimony trihalide solutions which are obtained after reduction are used directly for producing lead chromate pigments.

Another method provides a non-aqueous work-up procedure. Such a process is described in U.S. Pat. No. 3,760,059. In this procedure an equal volume of trichloroethylene is added to the solution containing antimony halide catalyst and organic impurities, and the mixture is heated in an autoclave. The resulting antimony trichloride, which is crystalline and anhydrous, can be separated from the organic constituents by suction filtering, and if desired, can be processed to produce antimony pentachloride, which then can be re-used as a catalyst. However, the addition of a considerable quantity of trichloroethylene which is necessary in this process (other olefins, apart from perchloroethylene, have proved unusable) leads to a correspondingly higher occurrence of unwanted byproducts having high boiling points.

SUMMARY OF THE INVENTION

It is the object of the present invention to provide an improved method for working up inactive solutions containing antimony halide catalysts and organic impurities which overcomes the drawbacks of the methods known from the prior art.

Another object of the invention is to provide a method for working up inactive solutions containing antimony halide catalysts and organic impurities which is uncomplicated and which can produce high purity, anhydrous antimony halides with only a few process steps.

A further object of the invention is to provide a method for working up inactive solutions containing antimony halide catalysts and organic impurities which decreases the corrosive stress on the apparatus which is used.

It is also an object of the invention to provide a method for working up inactive solutions containing antimony halide catalysts and organic impurities which does not produce unwanted byproducts.

Yet another object of the invention is to provide a method for working up inactive solutions containing antimony halide catalysts and organic impurities which can be carried out in available apparatus.

These and other objects are achieved by providing a method of working up inactive solutions containing antimony pentahalide catalysts and organic impurities, said method comprising adding elemental antimony to the solution and allowing the added antimony and the antimony pentahalide to react to produce antimony trihalide, crystallizing the antimony trihalide, and separating the organic impurities from the resulting crystalline antimony trihalide.

DETAILED DESCRIPTION OF PREFERRED EMBODIMENTS

The method according to the invention for working up inactive solutions containing antimony halide catalysts and organic impurities is characterized in that elemental antimony is added to this solution and the organic impurities are separated from the resulting crystalline antimony trichloride.

According to the method of the invention, inactive solutions containing antimony halide catalysts and organic impurities can be worked up as they occur during the fluorination of halogenated hydrocarbons, particularly chlorinated hydrocarbons, with anhydrous hydrogen fluoride.

In principle, the method according to the invention is suitable for working up antimony halide catalysts containing organic impurities such as occur during the fluorination of any halogenated hydrocarbons, such as more or less long-chained aliphatic, aromatic and aralipbatic compounds, with anhydrous hydrogen fluoride.

For instance, the method according to the invention is well suited for working up inactive solutions containing antimony pentahalide catalyst and organic impurities such as occur during the fluorination of aliphatic chlorinated hydrocarbons, in particular having one or two carbon atoms, by means of anhydrous hydrogen fluoride. It is especially suitable for working up the solutions which occur during the corresponding fluorination of $CCl_4$ to $CFCl_3$ or $CF_2Cl_2$, of $CHCl_3$ to $CHClF_2$, or of $C_2Cl_6$ to $C_2Cl_3F_3$ using anhydrous hydrogen fluoride.

Such solutions contain inorganic and organic compounds. The majority of the inorganic compounds is usually formed by antimony pentahalide, which is present primarily as antimony pentachloride. Furthermore, they usually contain a small quantity of trivalent antimony, predominantly in the form of antimony trichloride. Furthermore, they may contain fluoride as well as metal salts which come from corroded reactor material.

The absolute content of organic compounds in the catalyst solutions depends in particular on the length of use in the respective process. Usually, the solutions which are to be worked up in the method according to the invention contain up to 50% by weight organic constituents. The composition of these organic constituents depends on the production process in which the solution was produced.

For instance, the solutions which are to be worked up and are produced when $CHClF_2$ is produced from $CHCl_3$ contain constituents having higher boiling points such as $C_2Cl_5F$, $C_2H_2Cl_4$, $C_2Cl_6$ and other constituents having higher boiling points which are produced in undesired side reactions.

In the method according to the invention, no water is added during working-up. In a preferred embodiment, moisture is excluded. For this purpose, the method according to the invention may be performed in apparatus which is provided with a closure which permits pressure equalization with the environment, but prevents the entry of moisture from the environment. Such closures are known to persons skilled in the art. For instance, gas scrubbers containing conventional drying agents are suitable. Sulfuric acid preferably may be used as a drying agent. If desired, it is also possible to operate in an inert gas atmosphere, with noble gases or fluorochlorohydrocarbons or fluorohydrocarbons also being suitable as the inert gas as well as nitrogen.

The method according to the invention for working up inactive solutions containing antimony halide catalysts and organic impurities provides for elemental antimony to be added to this solution.

For this purpose, the antimony may, for instance, be placed in a reactor, and the solution can be metered into the reactor. This process variant has the advantage that it is particularly simple to carry out technically. In another process variant, the organic solution is poured into the reactor, and elemental antimony is metered into the solution. This variant is more expensive in technical terms than the alternative described above, but does have the advantage that the quantity of elemental antimony can be calculated simply and can be adapted in quantity to the respective solution which is to be worked up. The method according to the invention can be performed successfully using either variant.

The elemental antimony can be used in pieces of greater or lesser size up to a weight of 25 kg or more. It can also be used in the form of smaller particles. For instance, powdered antimony having a particle size of 0.1 to 1 mm is suitable. It is possible to suspend the antimony in a liquid which is inert (to antimony halides as well), for instance a fluorinated or chlorofluorinated hydrocarbon, and to use it as a suspension. However, this is not necessary and also is not considered especially advantageous.

Antimony trichloride is formed in an exothermic proportionating reaction from the added antimony and the antimony pentachloride present in the solution which is to be worked up by reduction of the pentavalent antimony. The resulting antimony trichloride crystallizes out of the solution upon cooling. The organic compounds are separated from the crystallized antimony trichloride according to known methods of solid/liquid phase separation. This may occur in a simple manner by decanting the liquid phase, by filtering the liquid off with suction, or by aspirating the liquid off.

The addition of the elemental antimony to the solution may be carried out at such a solution temperature that antimony trichloride crystallizes out during the addition of antimony. This may be achieved, for instance, by continuous cooling of the organic solution or by very slow combining of the constituents, so that the temperature of the organic solution is kept below the temperature at which antimony trichloride melts. This process is possible, but not very advantageous.

It has been shown that antimony trichloride crystallizes out as a covering layer on the elemental antimony and in this manner prevents the further reduction of the remaining antimony.

A preferred embodiment of the method according to the invention is therefore characterized in that while elemental antimony is added to the organic solution, the solution is maintained at such a temperature that the resulting antimony trichloride does not crystallize out. In a particularly preferred embodiment of the method according to the invention, after the addition of the elemental antimony has been completed, the organic solution is maintained during the reaction phase, and if desired also during a postreaction phase, at such a temperature that the resulting antimony trichloride does not crystallize out. Such a postreaction phase may last up to 30 hours, preferably from 12 to 24 hours.

The temperature at which the organic solution must be maintained in order to prevent antimony trichloride from crystallizing out may vary slightly depending on the origin of the solution and the organic and inorganic constituents contained in each case. Since chemically pure antimony trichloride melts or crystallizes at about 73° C., it is recommended to maintain the organic solution at a temperature in the range from about 65° C. to about 100° C. during the addition of antimony and optionally during a subsequent reaction phase. However, if desired, antimony trichloride which has crystallized out can be returned to the liquid phase by raising the temperature.

The method according to the invention may be performed at a pressure of 0.1 to 6 bar, preferably 0.5 to 3 bar.

While the elemental antimony is being added to the organic solution, and if desired also during a subsequent reaction phase, it is advantageous to mix the solution thoroughly, for instance with an appropriately high power stirrer.

The amount of elemental antimony which is to be used should advantageously be from about 0.5 mole to about 1 mole of antimony per mole of antimony pentachloride in the solution which is to be worked up. Desirably from about 0.6 to about 0.9 mole, particularly preferably from about 0.7 mole to about 0.8 mole, of elemental antimony is used per mole of antimony pentachloride. The total quantity of elemental antimony to be provided can be determined by analytical determination of the antimony pentahalide content of the solution which is to be worked up. The analysis is performed iodometrically. Advantageously, the course of the reaction is monitored by periodically removing a sample from the organic solution and analytically determining the content of antimony pentachloride which is still present.

After the addition of antimony has ended and if desired after a subsequent reaction phase, the solution which is to be worked up is brought to ambient temperature, for instance to temperatures between about 12° C. and about 25° C. This may take place by simply allowing the solution to stand at ambient temperature or alternatively by cooling, for instance with cooling water. In the course of the cooling process, crystalline antimony trichloride is formed, from which, as already described, the now substantially antimony-free organic phase can be separated, for instance by decanting, suction filtering, or aspirating off. The antimony trichloride which has crystallized out is already relatively pure (e.g. 95% pure) and may, for instance, be chlorinated, and the resulting antimony pentachloride then can be re-used as a catalyst in the fluorination process.

In a preferred embodiment, the antimony trichloride which has crystallized out is subjected to subsequent purification. This may take place in known manner, for instance by heating in inert solvents to dissolve the crystals, cooling the resulting solution, and separating recrystallized antimony trichloride from the cool solvent. If desired, it is possible to dry the antimony trichloride in a vacuum. Carbon tetrachloride is particularly suitable as a solvent for the subsequent purification. The resulting antimony trichloride contains only small amounts of impurities (e.g., it is more than 98% pure). If desired, the degree of purity can be increased even further by repeating the recrystallization and/or by distillation.

The resulting antimony trichloride can be used as such, for instance as a catalyst for organic syntheses, as an etching agent, or as a tanning additive.

Preferably the resulting antimony trichloride is reacted with elemental chlorine to produce antimony pentachloride. For this purpose, the antimony trichloride is reacted with elemental chlorine at a temperature in the range from about 20° C. to about 100° C. The chlorine is employed in the stoichiometrically required amount or in a slight excess. The chlorination may take place at a pressure in the range from about 0.5 atmospheres (absolute) to about 6 atmospheres (absolute). The resulting antimony pentachloride can be purified still further by distillation. It can be used as a catalyst for fluorination reactions.

If desired, the chlorination of antimony trichloride with chlorine may be carried out in the presence of a solvent which is inert to chlorine, antimony trichloride and antimony pentachloride under the reaction conditions which are used. Halogenated organic solvents such as chloroform, carbon tetrachloride, or chlorofluorohydrocarbons are highly suitable. The solvent may be present in a quantity of up to 25% by weight relative to the antimony trichloride which is used.

The solution of antimony pentachloride in the solvent used which is obtainable after chlorination can be used again as a catalyst for fluorination reactions. In this case, it is of course particularly advantageous if the solvent used during chlorination is at the same time the starting compound or the product of the fluorination reaction in which the solvent-containing antimony pentachloride is to be used as a catalyst. Thus, for instance, chloroform is the solvent which is advantageously used when the antimony pentachloride prepared in the presence thereof is to be used as a catalyst in the fluorination of chloroform.

The method according to the invention has surprising advantages:

Working up the inactive antimony halide catalyst solutions is uncomplicated, and it is possible to obtain anhydrous antimony halides of high purity with only a few process steps.

The corrosive stress on the apparatus which is used is less than has been customary in the prior art.

No unwanted byproducts are produced.

The solution can be worked up in the reactor system of the factory used to produce fluorinated compounds.

The following illustrative example is intended to explain the method of the invention in further detail without restricting its scope.

EXAMPLE a) Apparatus

A cylindrical reactor having an internal volume of 1050 ml and an internal diameter of 9.6 cm was used. The reactor wall was constructed as a double shell and consequently could be liquid-cooled or liquid-heated. The reactor was equipped with a device for introducing a solid, and was provided with a stirrer and a high-capacity cooler (multiple coil condenser). A safety washing bottle filled with sulfuric acid permitted pressure compensation with the surrounding atmospheric pressure, but prevented moisture from entering. Any waste gases produced were released into the environment through a waste gas scrubber, filled with aqueous potassium hydroxide solution.

b) Performance of the method

The inactive antimony catalyst solution was first analyzed. The antimony analyses were performed volumetrically with potentiometric indication (Redox measuring chain). Titration agents were n/10 (i.e. 0.1-normal) sodium thiosulfate solution and n/10 (i.e. 0.1-normal) potassium bromate solution. The analyses yielded the following values (the numerical data relate in each case to % by weight).

TABLE 1

| Inorganic Components: | | Organic Components: | |
|---|---|---|---|
| Total Antimony | 25.0 | Low boiling compounds (CFCl$_3$, CF$_2$Cl$_2$, CHFCl$_2$) | 10.7 |
| Sb$^I$ | 23.4 | | |
| Sb$^{III}$ | 1.6 | CH$_2$Cl$_2$ | 0.6 |
| Arsenic | 0.2 | CHCl$_3$ | 5.3 |
| Fluorine | 1.0 | C$_2$Cl$_4$F$_2$ | 0.7 |
| Chlorine | 33.1 | C$_2$Cl$_5$F | 5.0 |
| Total Inorganic Comp. | 59.3 | C$_2$H$_2$Cl$_4$ | 11.6 |
| | | C$_2$Cl$_6$ | 0.3 |
| | | Unidentified high boiling | 6.5 |
| | | Total Organic Components | 40.7 |

The density of the solution was approximately 2 g/cm$^3$.

500 ml of the organic solution which was to be worked up were poured into the reactor and heated to approximately 65° C. The total quantity of the antimony to be used was 183 g (approximately 1.5 mole) and was therefore somewhat greater than the quantity which was stoichiometrically necessary for complete reaction of the analytically determined pentavalent antimony (antimony (V) content in the solution: 230.5 g, corresponding to 1.89 mole; stoichiometrically necessary amount of elemental antimony: 153.7 g).

The elemental antimony, which was used in powder form, was introduced into the organic solution in portions via a flexible hose connection from a receptacle connected in gas-tight manner to the reactor, whereupon an exothermic reaction took place in the organic solution. The addition of the elemental antimony took place in such a manner that approximately 15% by weight of the total quantity of the antimony was added within about two hours, and after another four hours, 60% by weight was added. After a total time of six hours, the antimony had been completely added. After the addition of antimony had ended, the solution was kept for another five hours at a temperature of 70° C. Before cooling for crystallization purposes, approximately 100 ml carbon tetrachloride were added to the solution. Then the reactor with its contents was allowed to cool to ambient temperature overnight. During the cooling process, antimony trichloride crystallized out on the reactor walls. A dip tube was inserted into the reactor, and the liquid phase was withdrawn by suction (quantity withdrawn: 337 g). 50 ml carbon tetrachloride were added to the crystalline residue in the reactor, the residue was melted and re-crystallized by cooling to ambient temperature. Again the liquid phase was withdrawn by suction using means of a dip tube inserted into the reactor (quantity withdrawn: 84 g).

The crystalline antimony trichloride remaining in the reactor was 99% pure. The yield was 92% of the theoretical yield.

c) Processing antimony trichloride to regenerate antimony pentachloride 100 ml chloroform was added to the crystalline antimony trichloride obtained in the reactor in step (b). Chlorine gas was introduced into the liquid phase through a dip tube. The temperature of the solution, which was initially about 20° C., was gradually brought to about 76° C. by the reaction heat and additional heating. The chlorination was stopped when elemental chlorine was detectable in the downstream gas scrubber, which contained potassium iodide. After chlorination, the liquid reactor contents were again withdrawn using a dip tube. 1202 g of a solution were obtained which consisted substantially of antimony pentachloride (content: 76.2% by weight) and chloroform (content: 23.6% by weight). The impurity content, which predominantly consisted of trivalent antimony, was less than 0.2% by weight.

The resulting extremely pure solution was highly suitable as a catalyst for fluorination processes using hydrogen fluoride, in particular for fluorinating chloroform using anhydrous hydrogen fluoride.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. A method for working up inactive solutions containing antimony pentahalide catalysts and organic impurities, said method comprising adding elemental antimony to the solution and allowing the added antimony and the antimony pentahalide to react to produce antimony trihalide, crystallizing the antimony trihalide, and separating the organic impurities from the resulting crystalline antimony trihalide.

2. A method according to claim 1, wherein said antimony trihalide is antimony trichloride.

3. A method according to claim 1, wherein moisture is excluded.

4. A method according to claim 1, wherein during the addition of elemental antimony to the solution, the solution is maintained at a temperature sufficient to prevent precipitation of the resulting antimony trihalide.

5. A method according to claim 4, wherein the solution is maintained in the temperature range from about 65° C. to about 100° C.

6. A method according to claim 1, wherein during the reaction of elemental antimony with the pentavalent antimony, the solution is maintained at a temperature sufficient to prevent precipitation of the resulting antimony trihalide.

7. A method according to claim 6, wherein the solution is maintained in the temperature range from about 65° .C to about 100° C.

8. A method according to claim 1, wherein the method is carried out at a pressure in the range from about 0.1 bar to about 6 bar.

9. A method according to claim 8, wherein the method is carried out at a pressure in the range from about 0.5 bar to about 3 bar.

10. A method according to claim 1, wherein about 0.5 to about 1 mole of elemental antimony is used per mole of antimony pentahalide contained in the inactive catalyst solution.

11. A method according to claim 10, wherein about 0.6 to about 0.9 mole of elemental antimony is used per mole of antimony pentahalide contained in the inactive catalyst solution.

12. A method according to claim 2, further comprising the step of purifying the resulting crystalline antimony chloride.

13. A method according to claim 2, further comprising reacting the resulting antimony trichloride with elemental chlorine to produce antimony pentachloride.

14. A method according to claim 13, wherein said antimony trichloride is reacted with elemental chlorine in a halogenated organic solvent.

15. A method according to claim 1, wherein said inactive solution is a solution of antimony pentahalide catalyst and organic impurities produced during fluorination of a halogenated hydrocarbon with anhydrous hydrogen fluoride.

16. A method according to claim 15, wherein said halogenated hydrocarbon is a chlorinated hydrocarbon.

17. A method according to claim 1, wherein said antimony trihalide is crystallized by cooling the reaction solution.

* * * * *